(12) United States Patent
Wen et al.

(10) Patent No.: US 11,738,055 B2
(45) Date of Patent: Aug. 29, 2023

(54) CORAL COMPOSITE EXTRACT, COMPOSITION INCLUDING THE SAME AND METHOD OF PRODUCING THE SAME

(71) Applicant: NATIONAL SUN YAT-SEN UNIVERSITY, Kaohsiung (TW)

(72) Inventors: Zhi-Hong Wen, Kaohsiung (TW); Ping-Jyun Sung, Checheng Township (TW); Han-Chun Hung, Kaohsiung (TW); Chun-Hong Chen, Kaohsiung (TW); Yu-Chia Chang, Kaohsiung (TW)

(73) Assignee: NATIONAL SUN YAT-SEN UNIVERSITY, Kaohsiung (TW)

( * ) Notice: Subject to any disclaimer, the term of this patent is extended or adjusted under 35 U.S.C. 154(b) by 161 days.

(21) Appl. No.: 17/354,358

(22) Filed: Jun. 22, 2021

(65) Prior Publication Data

US 2021/0308194 A1 Oct. 7, 2021

Related U.S. Application Data

(62) Division of application No. 16/577,422, filed on Sep. 20, 2019, now Pat. No. 11,065,282.

(30) Foreign Application Priority Data

Dec. 14, 2018 (TW) .................................. 107145343

(51) Int. Cl.
*C07D 307/77* (2006.01)
*A61K 35/614* (2015.01)
*A61K 8/96* (2006.01)

(52) U.S. Cl.
CPC ............ *A61K 35/614* (2013.01); *A61K 8/965* (2013.01); *A61K 2236/331* (2013.01)

(58) Field of Classification Search
CPC .................................................... C07D 307/77
See application file for complete search history.

(56) References Cited

U.S. PATENT DOCUMENTS

| 8,530,513 B1 | 9/2013 | Sheu et al. |
| 2014/0294745 A1 | 10/2014 | Sung et al. |
| 2017/0157084 A1 | 6/2017 | Wen et al. |

FOREIGN PATENT DOCUMENTS

| CN | 1948302 A | 4/2007 |
| CN | 102675252 A | 4/2007 |
| CN | 101265248 A | 9/2008 |
| CN | 104095883 A | 10/2014 |

(Continued)

OTHER PUBLICATIONS

Kwak et al., "Milolides, new briarane diterpenoids from the Western Pacific octocoral Briareum stechei," J Nat Prod 64:754-760, 2001.*

(Continued)

*Primary Examiner* — Rosanne Kosson (57) ABSTRACT

The present invention relates to a coral composite extract, a composition including the same and a method of producing the same. The coral composite extract includes at least two briarane-type diterpenoid compounds from corals of *Briareum violaceum, B. excavatum* and *B. stechei*, thereby being applied as an effective ingredient of a skin external use composition, a cosmetic composition and a medicinal composition.

3 Claims, 5 Drawing Sheets

(56) References Cited

FOREIGN PATENT DOCUMENTS

| | | |
|---|---|---|
| CN | 104387403 A | 3/2015 |
| CN | 106822093 A | 6/2017 |
| CN | 108640890 A | 10/2018 |
| CN | 108653368 A | 10/2018 |
| JP | 2007523029 A | 8/2007 |
| KR | 20180060754 A | 6/2018 |
| TW | I344960 B | 12/2009 |
| TW | I353355 B | 12/2009 |
| TW | I364283 B | 6/2010 |
| TW | I429431 B | 2/2011 |
| TW | I398247 B1 | 4/2012 |
| TW | I398257 B2 | 7/2012 |
| TW | I487539 B | 10/2014 |
| TW | I602565 B | 6/2017 |
| TW | I627953 B | 10/2017 |
| TW | I604841 B | 11/2017 |
| TW | I627952 B | 7/2018 |

OTHER PUBLICATIONS

Su et al., "Briarane diterpenoids isolated from octocorals between 2014 and 2016," Marine Drugs 15(44):1-11, 2017.*

Chavan, Jaykumar J., et al., "Optimization of Extraction Techniques and RP-HPLC Analysis of Antidiabetic and Anticancer Drug Mangiferin from Roots of 'Saptarangi' (*Salacia chinensis* L.)", Journal of Liquid Chromatography & Related Technologies, 38: 963-969, 2015.

Chen, Bo-Yuan, "Studies on the chemical constituents from a cultured octocoral Briareum excavatum", full text and pp. 11, 14, 29 (for Structure No. 50-51, 73, 198), Thesis submitted to the Graduate Institute of Marine Biology, National Dong Hwa University, Taiwan, R.O.C., Jan. 2010.

Dhanani, Tushar, et al., "Effect of extraction methods on yield, phytochemical constituents and antioxidant activity of Withania somnifera", Arabian Journal of Chemistry, 2017, 10, S1193-S1199.

Kwak, Jong Hwan, et al., "Milolides, New Briarane Diterpenoids from the Western Pacific Octocoral Briareum stechei", Journal of Natural Products, May 30, 2001, pp. 754-760, vol. 64, No. 6.

Lin, Yen-You, et al., "Anti-Inflammatory and Analgesic Effects of the Marine-Derived Compound Excavatolide B Isolated from the Culture-Type Formosan Gorgonian Briareum excavatum", Marine Drugs, Apr. 27, 2015, pp. 2559-2579, vol. 13.

Sheu, Jyh-Horng, et al., "Novel Cytotoxic Diterpenes, Excavatolides A-E, Isolated from the Formosan Gorgonian Briareum excavatum", Journal of Natural Products, Apr. 10, 1998, pp. 602-608, vol. 61, No. 5.

Su, Yin-Di, et al., "Briarenolides U-Y, New Anti-Inflammatory Briarane Diterpenoids from an Octocoral Briareum sp. (Briareidae)", Marine Drugs, Dec. 3, 2015, pp. 7138-7149, vol. 13.

Su, Yin-Di, "Studies on the Chemical Constituents and Their Biological Activities from the Fomnosan Corals *Briareum* sp. and *Pinnigorgia* sp.", Doctorate Dissertation of Deparlnent of Marine Biotechnology and Resources, National Sun Yat-sen University, Taiwan, R.O.C., Feb. 2016.

Tsai, Tsung-Chang, et al., "Briaviolide Q, a New Briarane from the Cultured Briareum violaceum", Natural Product Communications, Aug. 30, 2018, pp. 1235-1237, vol. 13, No. 10.

Vale, Maria G.R., et al., "Extraction of Organic Material in Mineral Coal by Using Supercritical Fluid Extraction, Soxhlet, and Sonication Methods", J. Microcolumn Separations, 10(3) 259-263 (1998).

Yao, Jia-Wen, et al., "2-Acetoxybriaranes from Briareum violaceum", Tetrahedron, May 27, 2019, pp. 3751-3757, vol. 75.

Kwak, Jong Kwan, et al., "Milolides G-N, New Briarane Diterpenoids from the Western Pacific Octocoral Briareum stechei", J. Nat. Prod. 2002, 65, 704-708.

Xu, Jing-Hao, et al., "Briaviolides K-N, New Briarane-Type Diterpenoids from Cultured Octocoral Briareium violaceum", Mar. Drugs 2018, 16, 75, pp. 1-13.

\* cited by examiner

CORAL COMPOSITE EXTRACT, COMPOSITION INCLUDING THE SAME AND METHOD OF PRODUCING THE SAME

CROSS-REFERENCE TO RELATED APPLICATION

This application is a Divisional Application of the U.S. application Ser. No. 16/577,422, filed Sep. 20, 2019, which claims priority to Taiwan Application Serial Number 107145343, filed Dec. 14, 2018, which is herein incorporated by reference in its entirety.

BACKGROUND

Field of Invention

The present invention relates to a marine natural extract. More specifically, the present invention relates to a coral composite extract, a composition including the same and a method of producing the same.

Description of Related Art

The oceans cover about 70% of the Earth's surface and are the origins where life is born and bred. In the evolution process, marine organisms produce secondary metabolites that are different from terrigenous natural compounds and have unique structures to be adapted to the stringent environments such as hypersaline, high-pressure and anoxic environments, and so on, so as to obtain advantages for survival and competition.

However, marine resources and bioecological environments suffer various levels of damages due to overexploitation and anthropogenic destruction of partial marine environment recently. How to make good use of marine resources is one of the research priorities under the premise of ecological conservation of marine environments.

Taiwan is an ideal place for further research focusing on the secondary metabolites produced by corals since the coral systems in the sea area around Taiwan are well-developed and contain various species. Under the point of view, extensive Taiwanese experience to breed corals should be applied not only in conserving the marine ecology and reducing the shock to the marine living resources, but also in developing naturally active compounds to promote the application of marine living resources.

SUMMARY

Accordingly, one aspect of the present invention is to provide a coral composite extract obtained from a coral starting material by a crude extraction step and a column chromatography step, and the coral composite extract includes at least two briarane-type diterpenoid compounds.

In another aspect, the invention provides a coral composite extract obtained from a coral starting material originated from *Briareum violaceum* by a crude extraction step and a column chromatography step, in which the coral composite extract includes excavatolide B (EXC-B) and EXC-Z.

In the other aspect, the invention provides a coral composite extract obtained from a coral starting material originated from *B. excavatum* by a crude extraction step and a column chromatography step, in which the coral composite extract includes EXC-B and EXC-C.

In the other aspect, the invention provides a coral composite extract obtained from a coral starting material originated from *B. stechei* by a crude extraction step and a column chromatography step, in which the coral composite extract includes brianolide (BR), briarenolide X (BR-X) and BR-W.

In the other aspect, the invention provides a composition including the aforementioned coral composite extract as an effective ingredient.

In the other aspect, the invention provides a method of producing the coral composite extract, which includes performing a crude extraction step and a column chromatography step on the coral starting material, so as to obtain the aforementioned coral composite extract.

According to the aforementioned aspect, the invention provides a coral composite extract. In an embodiment, the coral composite extract is obtained from a coral starting material by a crude extraction step and a column chromatography step, in which the coral starting material can include but be not limited to *B. violaceum, B. excavatum* and *B. stechei*. The aforementioned coral composite extract includes at least two briarane-type diterpenoid compounds, and the briarane-type diterpenoid compounds can be excavatolide B (EXC-B), EXC-C, EXC-Z, brianolide (BR), briarenolide X (BR-X), and BR-W, for example.

According to the aforementioned aspect, the invention further provides a coral composite extract. In one embodiment, the coral composite extract can be obtained from a coral starting material originated from *B. violaceum* by a crude extraction step and a column chromatography step, in which the aforementioned coral composite extract can include EXC-B and EXC-Z, for example.

According to the aforementioned aspect, the invention further provides a coral composite extract. In one embodiment, the coral composite extract can be obtained from a coral starting material originated from *B. excavatum* by a crude extraction step and a column chromatography step, in which the aforementioned coral composite extract can include EXC-B and EXC-C, for example.

According to the aforementioned aspect, the invention further provides a coral composite extract. In one embodiment, the coral composite extract can be obtained from a coral starting material originated from *B. stechei* by a crude extraction step and a column chromatography step, in which the aforementioned coral composite extract can include at least two of brianolide (BR), briarenolide X (BR-X), and BR-W.

According to the aforementioned aspect, the invention further provides a composition applying the aforementioned coral composite extract as an effective ingredient.

According to the aforementioned aspect, the invention further provides a method of producing a coral composite extract. In one embodiment, the method performs a crude extraction step with a first solvent on the coral starting material to obtain a crude extract at first. In the aforementioned embodiment, the coral starting material can be *B. violaceum, B. excavatum* or *B. stechei*, for example, and the first solvent can include water, alcohol solvent, ester solvent, alkane solvent, and ketone solvent.

Furthermore, a column chromatography step is performed on the aforementioned crude extract by conducting a gradient elution treatment with a chromatography column to obtain the coral composite extract. In the aforementioned embodiment, the gradient elution treatment can be conducted with a second solvent, in which the second solvent can include the aforementioned ester solvent and/or alkane solvent, the coral composite extract can include at least two briarane-type diterpenoid compounds, and the at least two briarane-type diterpenoid compound can include EXC-B, EXC-C, EXC-Z, BR, BR-X and BR-W.

In one embodiment of the invention, the aforementioned coral starting material can be lyophilized.

In one embodiment of the invention, the aforementioned crude extraction step can further include a combination of an ultrasonic treatment and/or a microwave extraction treatment.

In one embodiment of the invention, the aforementioned alcohol solvent can be methanol, ethanol, propanol and isopropanol, for example.

In one embodiment of the invention, the aforementioned ester solvent can be ethyl acetate, isopropyl acetate, butyl acetate, methoxyethanol acetate and ethoxyethanol acetate, for example.

In one embodiment of the invention, the aforementioned ketone solvent can be acetone, for example.

In one embodiment of the invention, the ester solvent of the aforementioned second solvent can be ethyl acetate, for example, and the alkane solvent of the second solvent can be n-hexane, for example.

In one embodiment of the invention, a concentration gradient (volume ratio) of n-hexane to ethyl acetate of the second solvent can be 100:0 to 0:100, for example, when conducting the aforementioned gradient elution treatment.

By applying the coral composite extract, the composition including the same and the method of producing the same of the present invention, the coral composite extract includes at least two briarane-type diterpenoid compounds and can be added to the composition as an effective ingredient.

BRIEF DESCRIPTION OF THE DRAWINGS

The invention can be more fully understood by reading the followed detailed description of the embodiment, with reference made to the accompanying drawings as follows.

DETAILED DESCRIPTION

Singular forms, "a", "an", and "the", as mentioned in the present invention also cover plural references, unless otherwise stated in the context. A value range (such as 10% to 11% of A) includes its upper and lower limits (i.e. 10%≤A≤11%) if not otherwise stated specially; the value range, for which if no lower limit is defined (such as B lower than 0.2%, or B below 0.2%), can have a lower limit of zero (i.e. 0%≤B≤0.2%). The aforementioned terms were used for illustrating and helping understand the present invention rather than limiting the scope thereof.

The invention provides a coral composite extract obtained from a coral starting material by a crude extraction step and a column chromatography step, and the coral composite extract includes at least two briarane-type diterpenoid compounds.

The "coral composite extract" mentioned in the present invention is obtained from the coral starting material by the crude extraction step and the column chromatography step. In one embodiment, the aforementioned coral starting material can include but be not limited to *Briareum violaceum, B. excavatum* and *B. stechei*.

In the embodiment, the obtained coral composite extract can include at least two briarane-type diterpenoid compounds. Here, the mentioned at least two briarane-type diterpenoid compounds are the two briarane-type diterpenoid compounds with the highest amounts of the coral composite extract instead of limiting the coral composite extract to only two briarane-type diterpenoid compounds. In the aforementioned embodiment, the briarane-type diterpenoid compounds can be excavatolide B (EXC-B), EXC-C, brianolide (BR), briarenolide X (BR-X) and BR-W, for example.

In one example, the aforementioned coral composite extract can be obtained from the coral starting materials originated from *B. violaceum* by the crude extraction step and the column chromatography step, and the coral composite extract includes EXC-B and EXC-Z.

In one example, the aforementioned coral composite extract can be obtained from the coral starting materials originated from *B. excavatum* by the crude extraction step and the column chromatography step, and the coral composite extract includes EXC-B and EXC-C.

In one example, the aforementioned coral composite extract can be obtained from the coral starting materials originated from *B. stechei* by the crude extraction step and the column chromatography step, and the coral composite extract includes BR, BR-X and BR-W.

Figure 1:
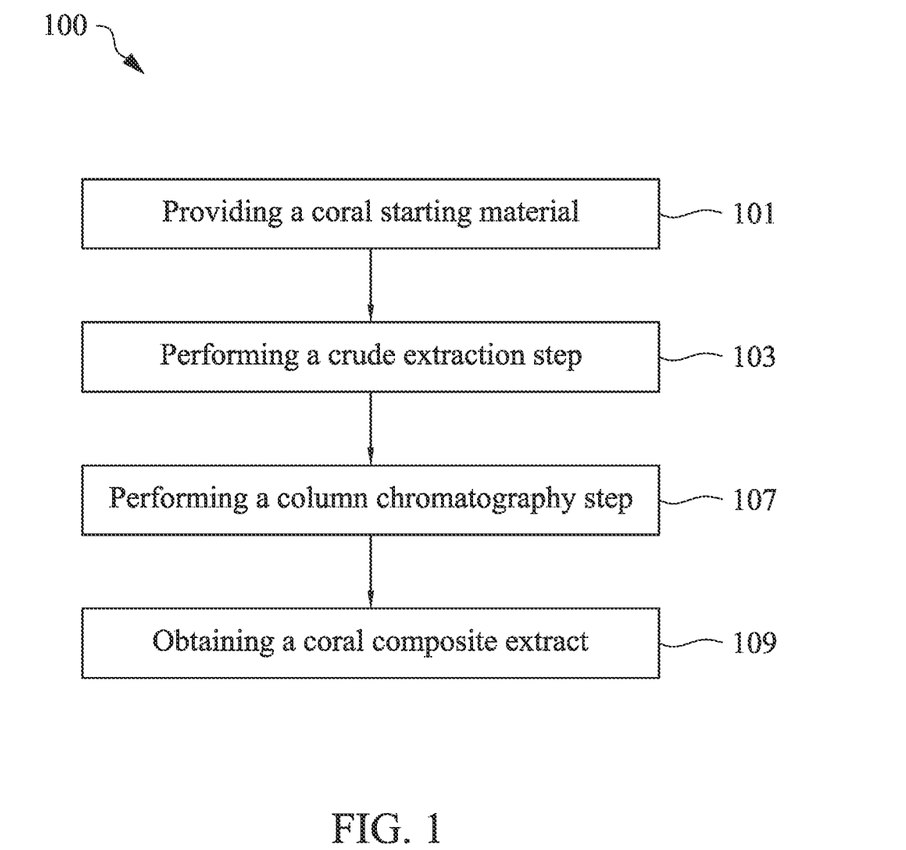
FIG. 1 is a partial flow chart showing the method of producing coral composite extract according to one embodiment of the present invention.

FIG. 1 is a partial flow chart showing the method 100 of producing coral composite extract according to one embodiment of the present invention. First, the coral starting material is provided as STEP 101 depicts. In one embodiment, the aforementioned coral starting material can include but be not limited to *B. violaceum, B. excavatum* and *B. stechei*. The aforementioned coral starting material can optionally be pretreated with known drying methods, such as atmospheric drying, vacuum drying, lyophilization, vacuum lyophilization, and so on, so as to remove moisture from the coral starting material without affecting and destroying the amount as well as the activity of the coral composite extract.

Next, as STEP 103 depicts, the crude extraction step is performed on the coral staring material to obtain a crude extract, in which a first solvent is applied. In one embodiment, there is no limitation of the kind of the first solvent. However, the one having a polarity index P' value closer to a polarity index P' value of the coral composite extract is the better. For example, a partition coefficient (log P) of EXC-B is about 0.9 and an octanol-water partition coefficient (Clog P) of EXC-B is about 3.5568. Therefore, the polarity index P' value of the first solvent can be 0.1 to 6.0, but 1.0 to 5.4 is better.

In the aforementioned embodiment, specific examples of the first solvent can include but be not limited to water, alcohol solvent, ester solvent, alkane solvent and ketone solvent. The alcohol solvent is short-chain alcohol, for example, alcohol having 1 to 3 carbon atoms, in which specific examples can be methanol, ethanol, propanol and isopropanol but not allyl alcohol and propargyl alcohol. The ester solvent can include but be not limited to ethyl acetate, methoxyethanol acetate and ethoxyethanol acetate. The alkane solvent can include but be not limited to n-hexane. The ketone solvent can include but be not limited to acetone, methyl ethyl ketone (MEK).

In the aforementioned embodiment, a solid-liquid ratio of the aforementioned coral starting material to the aforementioned first solvent is not limited. In one example, the solid-liquid ratio (g:mL) of the aforementioned coral starting material to the first solvent can be 1:1 to 1:20, for example. However, 1:1 to 1:15 is better, and 1:1 to 1:10 is much better.

In the aforementioned embodiment, the crude extraction step can be either conducted by the solvent extraction treatment with the first solvent along or the solvent extraction treatment in combination with an ultrasonic treatment and/or a microwave extraction treatment, or a supercritical extraction treatment with a mixture of the aforementioned alcohol solvent and a supercritical fluid. The aforementioned supercritical fluid can be carbon dioxide, for example.

In general, a boiling point of the aforementioned first solvent is lower than a melting point of the coral composite extract (about 224° C.). Thus, it is better that the ultrasonic treatment and/or the microwave extraction treatment are conducted under the temperature lower than the boiling point of the first solvent to perform the crude extraction step. In one specific example, the crude extraction step can be performed under the temperature lower than 156° C., 145° C., 100° C., 78° C. or 77° C. However, the temperature is not limited to the aforementioned examples but depends on the extraction solvent.

In the aforementioned embodiment, there is no specific limit on how many times the crude extraction step is performed. Rather, the crude extraction step can be performed once or repeated for many times to increase the yield of the crude extract. In one example, the crude extraction step can be repeated for once to 10 times, and preferably once to 6 times.

In the aforementioned embodiment, the coral starting material can include but be not limited to B. violaceum, B. excavatum and B. stechei. In one example, the coral starting material can be unprocessed or lyophilized.

However, as STEP 107 in FIG. 1 depicts, in one embodiment, after the aforementioned crude extraction step, the column chromatography step can be performed by conducting the gradient elution treatment on the crude extract with a chromatography column to obtain factions of the coral composite extract, as STEP 109 depicts.

In the aforementioned embodiment, the aforementioned chromatography column can be a commercially available silica chromatography column, and the aforementioned gradient elution treatment can be conducted with a second solvent including the aforementioned ester solution and/or alkane solution. In one example, the ester solvent of the second solvent can be ethyl acetate, and the alkane solvent of the second solvent can be n-hexane. A concentration gradient (volume ratio) of n-hexane to ethyl acetate of the second solvent for the gradient elution treatment can be 100:0 to 0:100, but 80:20 to 40:60 are preferred.

In some specific examples, an n-hexane to the ethyl acetate concentration gradient (volume ratio) of the second solvent can be 60:40 to 50:50, for example, for the gradient elution treatment conducted on the crude extract of the B. violaceum. In other specific examples, the concentration gradient (volume ratio) of n-hexane to ethyl acetate of the second solvent can be 80:20 to 70:30, for example, for the gradient elution treatment conducted on the crude extract obtained from B. excavatum. In other specific example, the concentration gradient (volume ratio) of the n-hexane and the ethyl acetate of the second solvent can be 70:30, for example, for the gradient elution treatment conducted on the crude extract of the B. stechei.

It should be supplemented that, in other embodiments, a lipid removal treatment can be optionally conducted after the crude extraction step (STEP 103 in FIG. 1) and/or together with the process of the column chromatography step (STEP 107 in FIG. 1) in the method 100 of producing the coral composite extract of the present invention. In the aforementioned example that the lipid removal treatment is conducted after the crude extraction step (STEP 103 in FIG. 1), the crude extract can be cold soaked in the ester solvent (for example, ethyl acetate) for precipitating lipid with the ester solvent so as to remove most of the lipid in the crude extract. On the other hand, in the example that the lipid removal treatment is conducted together with the column chromatography step (STEP 107 in FIG. 1), the crude extract can be filled in the chromatography column and be eluted with alkane solvent (such as n-hexane) and/or ester solvent (such as ethyl acetate) with lower polarities for the gradient elution treatment to remove most of the lipid in the crude extract, in which the volume ratio of the alkane solvent (such as n-hexane) and ester solvent (such as ethyl acetate) can be 100:0 to 95:5, for example.

In some embodiments, each aforementioned fractions obtained including the coral composite extract can be separated or combined together, and the second solvent therein is further remove by the known dehydration method (for example, vacuum concentration, lyophilization, spray drying, etc.) to obtain the coral composite extraction. Then, the obtained coral composite extract is found to have at least two briarane-type diterpenoid components, for example, EXC-B, EXC-C, EXC-X, BR, BR-X and BR-W, by analyzing with the known analytical method e.g., thin-layer chromatography (TLC), nuclear magnetic resonance spectroscopy (NMR), infrared spectroscopy (IR) and mass spectroscopy (MS), and so on.

It should be supplemented that, the obtained coral composite extract will not contain the at least two briarane-type aforementioned diterpenoid compounds if the starting coral material is not originated from the abovementioned specific species, or if the starting coral material is not extracted with the abovementioned crude extraction step and the column chromatography step.

In application, the abovementioned coral composite extraction can be applied as an effective ingredient in compositions, i.e., a skin external use composition, a cosmetic composition and a medicinal composition, etc. In one example, the aforementioned composition can be, for example, applied to the test part by smearing or covering, etc., and the formulation can be an emulsion, cream, hydrogel, gel, gel dressings, foam dressings, film dressings or any combination from above. In application, the effective dose of the coral composite extract in the aforementioned composition can be 0.001 mg/mL to 20 mg/mL, for example.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the followed claims.

Example 1: Preparing Coral Composite Extract

1. Coral Composite Extract Prepared from *Briareum violaceum*

Figure 2:
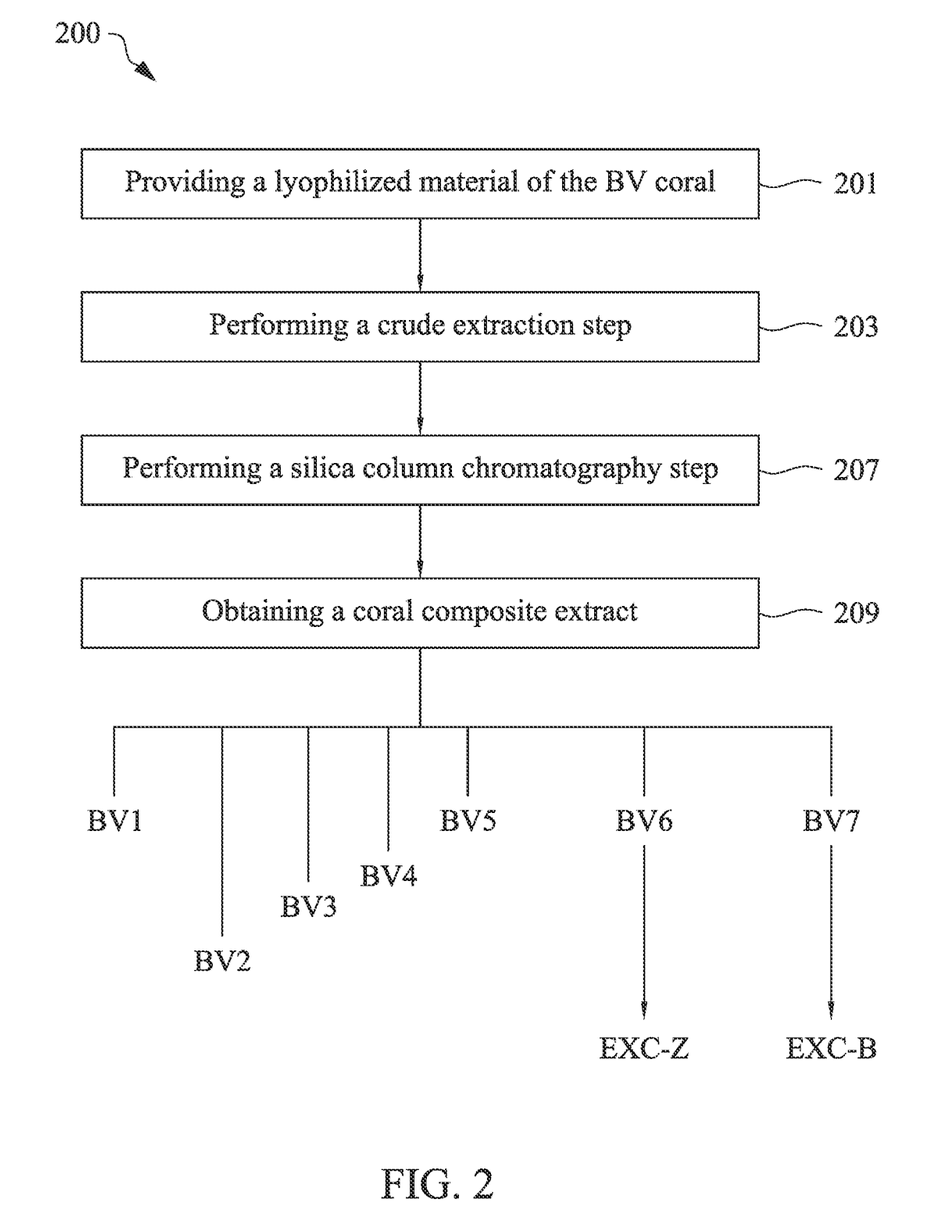
FIG. 2 is a partial flow chart showing the method of producing coral composite extract according to another embodiment of the present invention.

In the present embodiment, *Briareum violaceum* (BV) was applied as the coral stating material to obtain the coral composite extract. FIG. 2 showed the partial flow chart of the method 200 of producing coral composite extract according to another embodiment of the present invention. Firstly, as shown in STEP 201, the lyophilized material of the BV coral was provided, in which the original wet weight of the BV coral material was 231 g, and its lyophilized dry weight was 95 g. Next, as shown in STEP 203, the crude extraction step was performed on the lyophilized BV coral material by repeating the solvent extraction treatment with ethyl acetate (1000 mL) as the first solvent for 20 times, thereby obtaining the crude extract (3.3 g) in the ethyl acetate layer. Then, as shown in STEP 207, the column chromatography step was performed on the crude extract (i.e., the ethyl acetate layer) by conducting the gradient elution treatment with a commercial available chromatography column [in which the packing was silica gel (70-230 mesh, Merck)] and a second solvent as an eluent to obtain 7 fractions BV1 to BV7, in which the second solvent was a mixture of n-hexane and ethyl acetate with a concentration gradient (volume ratio) of 100:0 (i.e., pure n-hexane) to 95:5 (BV1, 0.11 g), 90:10 (BV2, 0.55 g), 80:20 (BV3, 0.20 g), 70:30 (BV4, 0.23 g), 60:40 (BV5, 0.83 g), 50:50 (BV6, 0.22 g) and 40:60 to 0:100 (i.e., pure ethyl acetate) (BV7, 1.04 g).

By analyzing the aforementioned fractions with TLC, NMR, IR, MS, and so on, it was found that fraction BV1 included lipid, and the fraction BV6 and the fraction BV7 included the coral composite extract, in which the fraction BV6 included 0.02 g of EXC-Z, while the fraction BV7 included 0.6 g of EXC-B, as shown in STEP 209.

2. Coral Composite Extract Prepared from *B. excavatum*

Figure 3:
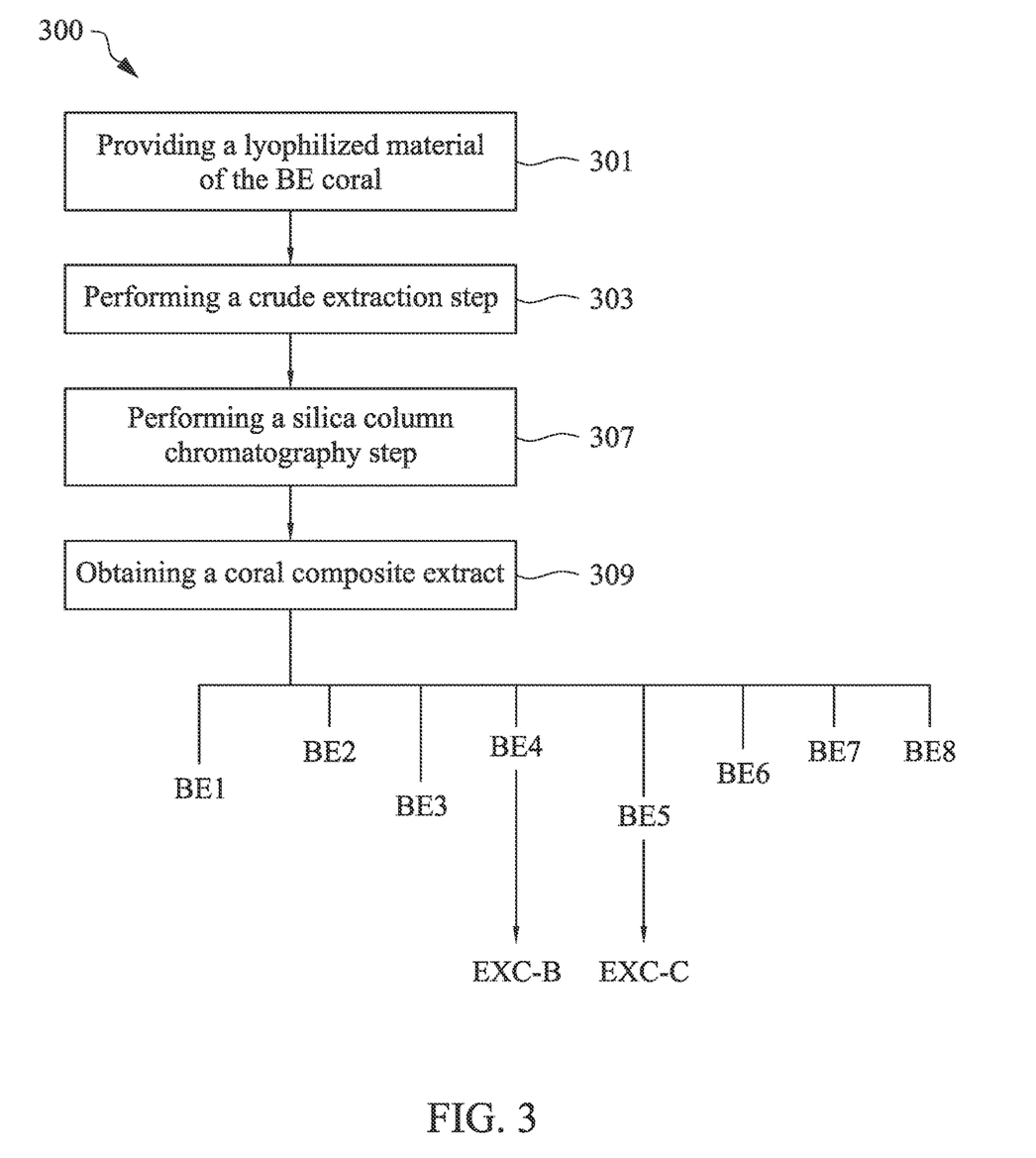
FIG. 3 is a partial flow chart showing the method of producing coral composite extract according to the other embodiment of the present invention.

In the embodiment, *B. excavatum* (BE) was applied as the coral starting material to obtain the coral composite extract. FIG. 3 showed the partial flow chart of the method 300 of producing the coral composite extract according to the other embodiment of the present invention. Firstly, as shown in STEP 301, the lyophilized BE coral material was provided, in which the lyophilized dry weight of the BE coral material was 1900 g. Next, as shown in STEP 303, the crude extraction step was performed on the lyophilized BE coral with ethyl acetate (2000 mL) as the first solvent for 20 times, in which the crude extraction step included the solvent extraction treatment or the solvent extraction treatment in combination with the ultrasonic treatment, thereby obtaining the crude extract (96.1 g) from the ethyl acetate layer.

Then, the crude extract (96.1 g) was cold soaked in ethyl acetate (800 mL) for precipitating lipid so as to remove most of the lipid (5.6 g) in the crude extract. After that, as shown in STEP 307, the column chromatography step was performed on the crude extract (i.e., the ethyl acetate layer, 90.5 g) with the same aforementioned commercial available chromatography column for conducting the gradient elution treatment on the crude extract with a second solvent as the eluent so as to obtain 8 fractions BE1 to BE8, in which the second solvent was a mixture of n-hexane and ethyl acetate with concentration gradient (volume ratio) of 100:0 (i.e., pure n-hexane) (BE1), 95:5 (BE2), 90:10 (BE3), 80:20 (BE4), 70:30 (BE5), 60:40 (BE6), 50:50 (BE7) and 40:60 to 0:100 (i.e., pure ethyl acetate) (BE8).

By analyzing the aforementioned fractions with TLC, NMR, IR, MS, and so on, it was found that the fraction BE1 and the fraction BE2 included lipid, and the fraction BE4 and the fraction BE5 included the coral composite extraction, in which the fraction BE4 included 16.2 g of EXC-B, while the fraction BE5 included 3.4 g of EXC-C, as shown in STEP 309.

Moreover, to evaluate the extraction efficiency of different extraction treatments, the aforementioned solvent extraction treatment could optionally apply with a commercially available stirring device, for example, Thermo hot-plate stirrer, (i.e., direct solvent extraction), which mixed first solvent at 150 rpm in the room temperature for 2 hours continuously with the coral starting material, which was then filtered and repeatedly extracted for five times.

For the solvent extraction treatment combining with the ultrasonic treatment, commercial available ultrasonic devices, for example, an ultrasonic device A (130 Watt Vibra-Cell Ultrasonics Processor, Cat. #VCX130, Sonics, Hsinchu, Taiwan, power consumption as 130 W, frequency as 20 kHz and dissipated power as 100%) and an ultrasonic device B (Cat. #DC900H, Delta, Taichung, Taiwan, power as consumption 900 W, frequency as 40 kHz and dissipated as power 100%) could be used. When using the ultrasonic device A, a treatment so-called ultrasonic homogenizer extraction proceeded every 10 sec with 1 second of break in a duration of 2 hours on the coral starting material, which was then filtered and repeatedly extracted with the first solvent for five times. When using the ultrasonic device B, a treatment so-called ultrasonic cleaner extraction proceeded in a duration of 2 hours on the coral starting material, which was then filtered and repeatedly extracted with the first solvent for five times. The table below showed the extraction rates of the aforementioned crude extraction step in different ways:

TABLE 1

|  | Ultrasonic homogenizer extraction | Ultrasonic cleaner extraction | Direct solvent extraction |
| --- | --- | --- | --- |
| Dry weights of the starting material | 300.15 g | 300.66 g | 300.39 g |
| Solid to liquid ratio (weight:volume) | 1:10 | 1:10 | 1:10 |
| Ethyl acetate layer extraction rate | 6.48% | 6.20% | 6.18% |
| Residue recovery rate | 90.96% | 92.32% | 90.11% |

Figure 5:
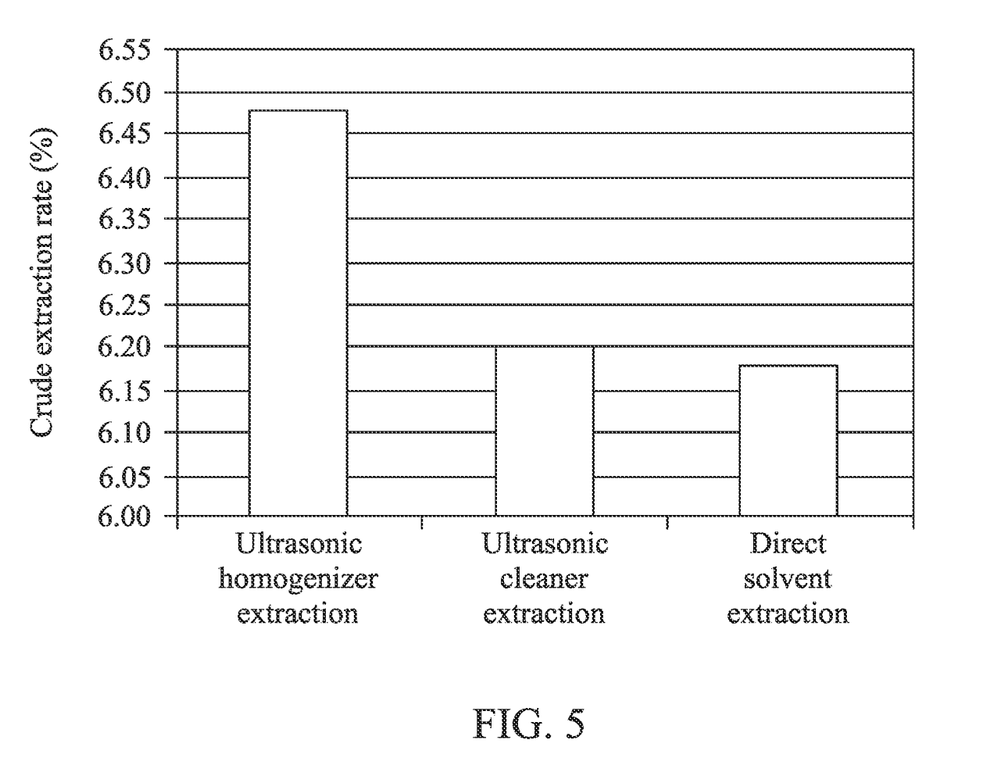
FIG. 5 is a bar chart of the extraction rate of the crude extract obtained by the crude extraction step in different ways according to TABLE 1.

Please refer to TABLE 1 and FIG. 5, which showed the extraction rate (TABLE 1) of the crude extract obtained by the crude extraction step in different ways and the bar chart thereof (FIG. 5). In FIG. 5, the vertical axial represented the extraction rate (%) of the obtained crude extract with the lyophilized dry weight considered as 100%.

Referring to Table 1 and FIG. 5, the solvent extraction treatment in combination with the ultrasonic treatment could indeed increase the extraction rate of the crude extract. Moreover, the extraction rate of the ultrasonic homogenizer extraction was higher than that of the ultrasonic cleaner extraction and the direct solvent extraction.

3. Coral Composite Extract Prepared from *B. stechei*

Figure 4:
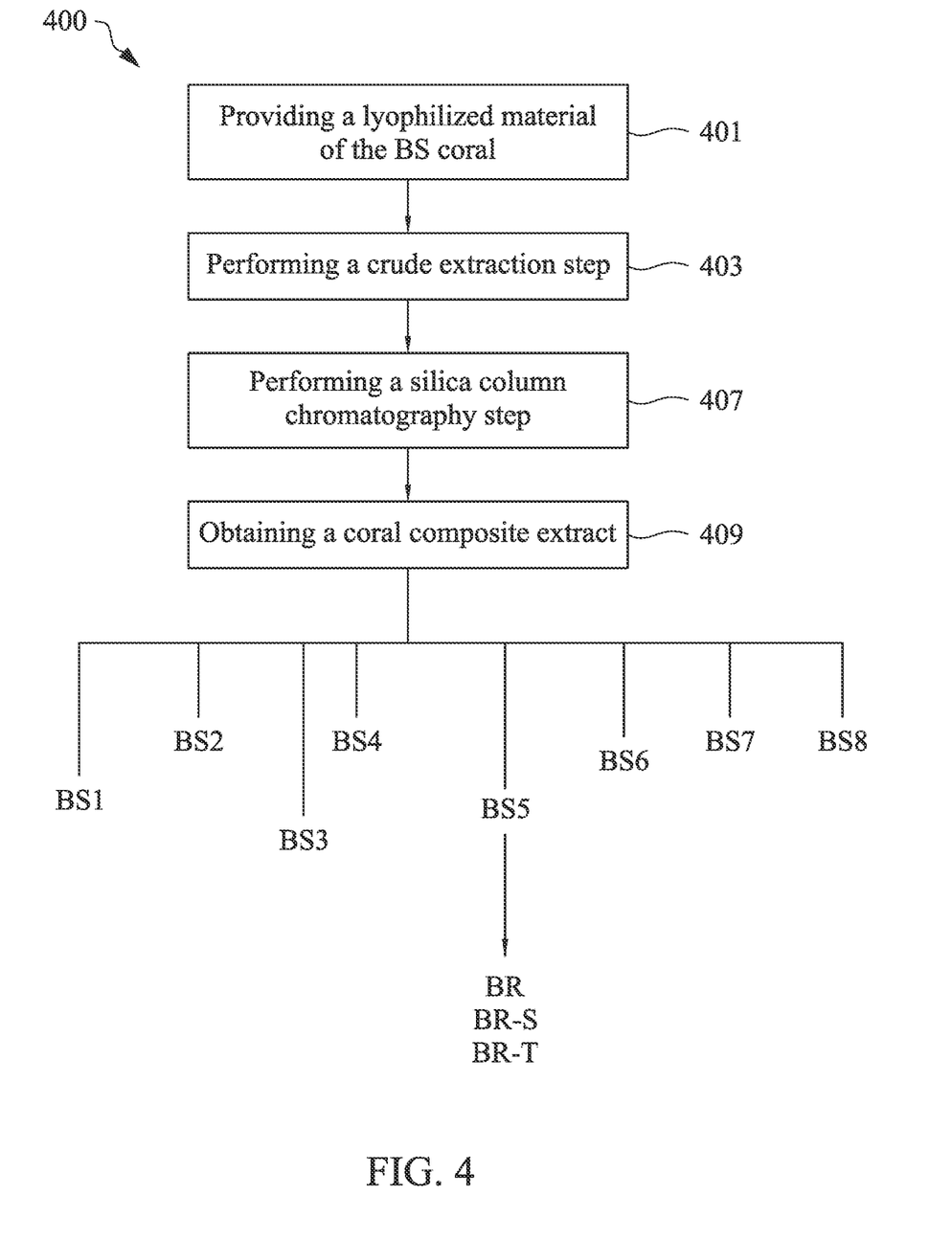
FIG. 4 is a partial flow chart showing the method of producing coral composite extract according to the other embodiment of the present invention.

In the embodiment, *B. stechei* (BS) was selected as the coral starting material to obtain the coral composite extract. FIG. 4 was the partial flow chart of the method 400 of producing coral composite extract according to the other embodiment of the present invention. Firstly, as shown in STEP 401, the lyophilized BS coral material was provided, in which the original wet weight of the BS coral material is 6320 g, and its lyophilized dry weight was 2780 g. Next, as shown in STEP 403, the crude extraction step was performed on the lyophilized BS coral material with ethyl acetate (3000 mL) as the first solvent for repeating the solvent extraction treatment for 20 times, thereby obtaining the crude extract (126.96 g) in the ethyl acetate layer. Then, the column chromatography step was performed on the crude extract (i.e., ethyl acetate layer) by performing the gradient elution treatment with the aforementioned commercial available chromatography column and the second solvent as the eluent on the crude extract to obtain 8 fractions BS1 to BS8, in which the second solvent was a mixture of n-hexane and ethyl acetate with the concentration gradient (volume ratio) of 100:0 (i.e., pure n-hexane) to 95:5 (BS1, 42.09 g), 90:10 to 80:20 (BS2, 3.81 g), 70:30 to 60:40 (BS3, 4.63 g), 50:50 to 40:60 (BS4, 14.71 g), 30:70 to 0:100 (i.e., pure ethyl acetate) (BE5, 25.89 g), 90:10 to 70:30 (BS6, 2.33 g), 50:50 (BS7, 7.23 g) and 30:70 to 0:100 (i.e., pure ethyl acetate) (BS8, 24.78 g).

By analyzing with TLC, NMR, IR, MS, and so on, it was found that the fraction BS1 and the fraction BS2 included lipid and the fraction BS5 included the coral composite extract containing 3.79 g BR (as shown in formula 1), 0.01 g BR-X (as shown in formula 2) and 0.02 g (shown in formula 3).

Formula 1

Formula 2

Formula 3

It should be supplemented that, the coral composite extract in this invention can be applied as an effective ingredient of compositions, for example, a skin external use composition, a cosmetic composition and a medicinal composition, etc.

In sum, although specific species of the corals, specific extraction methods and specific evaluation methods are shown in the present invention as examples to explain the coral composite extract, the composition including the same and the method of producing the same, it will be apparent to those skilled in the art that the present invention is not limited to what have mentioned. Without departing from the scope or spirit of the invention, it is intended that the present invention covers other coral species, methods for extraction and evaluation.

From the aforementioned embodiments, the advantages of the coral composite extract, the compositions including the same and the methods of producing the same are that the coral composite extract contains at least two briarane-type diterpenoid compounds and can be added to the composition as an effective ingredient.

Although the present invention has been described in considerable detail with reference to certain embodiments thereof, other embodiments are possible. Therefore, the spirit and scope of the appended claims should not be limited to the description of the embodiments contained herein.

What is claimed is:

1. A coral composite extract obtained from a *Briareum stechei* coral starting material by (i) a crude extraction step and (ii) a column chromatography step, wherein the crude extraction step comprises a solvent extraction treatment combined with an ultrasonic treatment, wherein the coral composite extract comprises at least two briarane-type diterpenoid compounds that are brianolide (BR) and briarenolide W (BR-W), and wherein the two briarane-type diterpenoid compounds are the two that are present in the highest amounts in the coral composite extract.

2. A composition comprising the coral composite extract of claim 1, wherein the coral composite extract is a therapeutically effective ingredient.

3. The composition of claim 2, wherein the composition is a cosmetic composition or a medicinal composition.

\* \* \* \* \*